United States Patent

Smith, Jr.

(10) Patent No.: US 7,119,244 B2
(45) Date of Patent: Oct. 10, 2006

(54) METHOD OF REMOVING ORGANIC SULFUR COMPOUNDS FROM ALKYLATE

(75) Inventor: Lawrence A. Smith, Jr., Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 11/034,460

(22) Filed: Jan. 13, 2005

(65) Prior Publication Data

US 2006/0155156 A1    Jul. 13, 2006

(51) Int. Cl.
  *C07C 2/62* (2006.01)
  *C10G 17/06* (2006.01)

(52) U.S. Cl. ............... 585/718; 585/719; 585/730; 585/731; 585/800; 208/224

(58) Field of Classification Search ......... 585/718, 585/800, 719, 730, 731; 208/224
  See application file for complete search history.

(56) References Cited

U.S. PATENT DOCUMENTS

| | | | |
|---|---|---|---|
| 2,091,917 A | 8/1937 | Fenske et al. ............... 196/46 |
| 2,472,578 A | 6/1949 | Ferris et al. ............... 196/13 |
| 2,859,260 A * | 11/1958 | Stiles ........................ 585/718 |
| 3,013,093 A | 12/1961 | Stiles ........................ 260/683.62 |
| 3,155,742 A | 11/1964 | Holzman et al. ...... 260/683.48 |
| 3,496,996 A | 2/1970 | Osdor ........................ 165/111 |
| 3,725,499 A | 4/1973 | Goldsby ................. 260/683.62 |
| 3,759,318 A | 9/1973 | Putney et al. ............... 165/108 |
| 3,839,487 A | 10/1974 | Clonts ................... 260/683.48 |
| 4,075,258 A | 2/1978 | Caulk et al. ........... 260/683.44 |
| 4,139,573 A | 2/1979 | Carson ................... 260/683.49 |
| 4,783,567 A | 11/1988 | Kocal ......................... 585/464 |
| 4,891,466 A | 1/1990 | Kocal ......................... 585/464 |
| 5,196,626 A | 3/1993 | Child et al. .................. 585/720 |
| 5,220,095 A | 6/1993 | Hommeltoft et al. ........ 585/720 |
| 5,345,027 A | 9/1994 | Child et al. .................. 585/720 |
| 5,420,093 A | 5/1995 | Joly et al. .................... 502/216 |
| 5,444,175 A | 8/1995 | Joly et al. .................... 585/714 |
| 5,785,933 A | 7/1998 | Cunningham et al. ....... 422/224 |
| 6,204,425 B1 | 3/2001 | Hommeltoft ................ 585/730 |
| 6,852,902 B1 | 2/2005 | Smith, Jr. .................... 585/718 |
| 6,858,770 B1 | 2/2005 | Smith, Jr. et al. ........... 585/720 |

* cited by examiner

*Primary Examiner*—Thuan Dinh Dang
(74) *Attorney, Agent, or Firm*—Kenneth H. Johnson

(57) ABSTRACT

A process for the removal of organic sulfur compounds, primarily oxygenated organic compounds, such as sulfates and sulfonic esters from a hydrocarbon liquid is disclosed which comprises contacting the hydrocarbon liquid with a coalescer comprising a mesh material which has been wetted by sulfuric acid. The hydrocarbon liquid may be the product from a sulfuric acid catalyzed alkylation process and contain sufficient sulfuric acid to remove the sulfates and sulfonic esters. Sulfuric acid may be added to the coalescer vessel counter current to the hydrocarbon liquid to improve the efficiency of the contacting and removal.

10 Claims, 1 Drawing Sheet

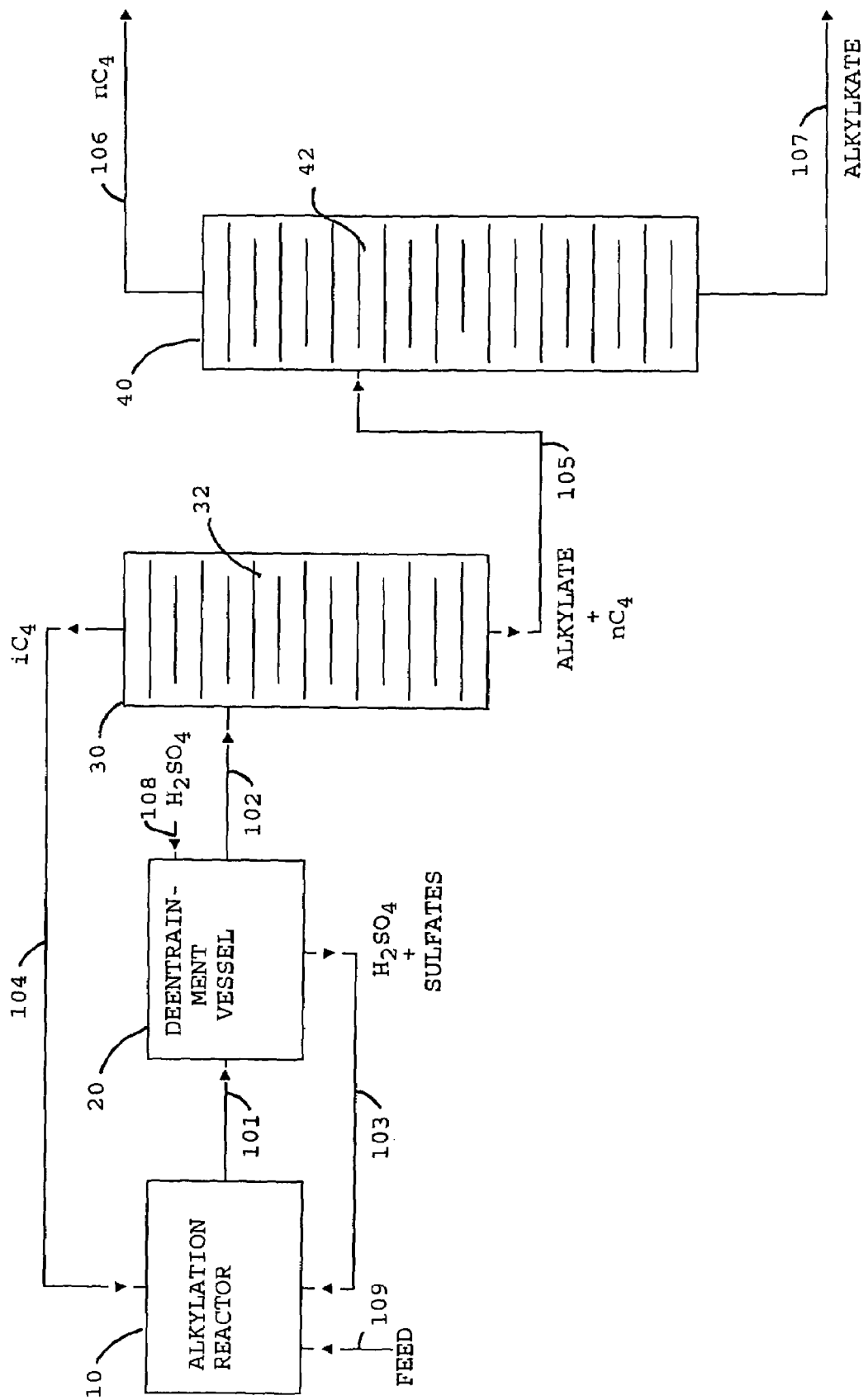

METHOD OF REMOVING ORGANIC SULFUR COMPOUNDS FROM ALKYLATE

BACKGROUND OF THE INVENTION

1. Field of the Invention

The present invention relates to the treatment of alkylate product from a process wherein normal olefins are reacted with isoalkanes in the presence of sulfuric acid to produce alkylate product. More particularly the invention relates to a process wherein the effluent from the alkylation reactor is passed through a deentrainment device to remove sulfuric acid by coalescence and concurrently treated to remove oxygenated organic sulfur compounds.

2. Related Information

In the petroleum refining industry, acid catalyzed alkylation of aliphatic hydrocarbons with olefinic hydrocarbons is a well known process. Alkylation is the reaction of a paraffin, usually isoparaffins, with an olefin in the presence of a strong acid which produces paraffins, e.g., of higher octane number than the starting materials and which boil in the range of gasolines. In petroleum refining the reaction is generally the reaction of a $C_2$ to $C_5$ olefin with isobutane.

In refining alkylations, hydrofluoric or sulfuric acid catalysts are most widely used under low temperature conditions. Low temperature or cold acid processes are favored because side reactions are minimized. In the traditional process the reaction is carried out in a reactor where the hydrocarbon reactants are dispersed into a continuous acid phase.

Although this process has not been environmentally friendly and is hazardous to operate, no other process has been as efficient and it continues to be the major method of alkylation for octane enhancement throughout the world. In view of the fact that the cold acid process continues to be the process of choice, various proposals have been made to improve and enhance the reaction and to some extent moderate the undesirable effects.

In the past the alkylate product has been washed with water or treated with caustic to remove or neutralize any carry over sulfuric acid. Both methods of treatment have drawbacks. When a water wash is used, there is some carryover of water to the distillation columns used to separate the alkylate from unreacted materials. This water dilutes any acid left and dissolves any sulfonates or sulfonic esters which cause corrosion problems. The caustic tends to produce salts which can foul downstream heat exchangers, especially the reboiler in the recovery columns.

Various solutions have been proposed to moderate the problems associated with cold acid reactions. U.S. Pat. No. 5,220,095 disclosed the use of particulate polar contact material and fluorinated sulfuric acid for the alkylation. U.S. Pat. Nos. 5,420,093 and 5,444,175 sought to combine the particulate contact material and the catalyst by impregnating a mineral or organic support particulate with sulfuric acid.

It is an advantage of the present invention that it overcomes the water/sulfuric acid carryover by a more effective process of acid/water separation and recovery.

SUMMARY OF THE INVENTION

Briefly the invention comprises removing the sulfuric acid from the alkylate by mechanical means instead of water wash or caustic treatment product prior to treatment to remove organic sulfur compounds, preferably oxygenated sulfur compounds, such as sulfates and sulfonic esters, by sorption. The preferred mechanical means comprises a vessel containing a coalescer material upon which the sulfuric acid impinges. The sulfuric acid, being much heavier than the hydrocarbon, falls out and may be removed by gravity. The alkylate product is concurrently treated to remove oxygenated organic sulfur compounds by adsorption on the coalescer packing which has been wetted by sulfuric acid. The extracted sulfate esters either decompose or return to the reactor by gravity with the disentrained sulfuric acid stream. Preferably the coalescer is wetted with sulfuric acid in order to remove oxygenated organic sulfur compounds, such as sulfate esters, sulfonates and sulfones with the detrained sulfuric acid. The wetting may occur from the detrained sulfuric acid, but preferably sulfuric acid is contacted with the hydrocarbon stream in the coalescer in countercurrent flow.

BRIEF DESCRIPTION OF THE DRAWING

The FIGURE is a simplified flow diagram of one embodiment of the invention.

DETAILED DESCRIPTION OF THE PREFERRED EMBODIMENT

The alkylate product to be treated may come from any cold acid alkylation process which uses sulfuric acid as the catalyst. Preferably, the fluid system comprises a liquid.

Typically the alkylate from the alkylation process contains some sulfuric acid as well as sulfonates and sulfonic esters which must be removed. Referring now to the FIGURE a simplified flow diagram of one embodiment is shown. Feed to the alkylation reactor which comprises $C_4$ alkanes and alkenes is via flow line 109. The alkylate is taken from alkylation reactor 10 via flow line 101 and fed to deentrainment vessel 20. Deentrainment vessel 20 contains a coalescer material upon which the sulfuric acid droplets impinge and fall out. The sulfuric acid and hydrocarbons in the alkylate product are practically insoluble in one another. The coalescer material is wetted by sulfuric acid in the stream and preferably by addition of sulfuric acid fed via flow line 108 countercurrent to hydrocarbon flow.

The coalescer comprises a conventional liquid-liquid coalescer of a type which is operative for coalescing vaporized liquids. These are commonly known as "mist eliminators" or "demisters". A suitable coalescer comprises a mesh such as a co-knit wire and polymeric material, such as fiberglass mesh. For example, it has been found that a 90 needle tubular co-knit mesh of wire and fiberglass such as manufactured by Amistco Separation Products, Inc. of Alvin, Tex. or ACS Industries LLC of Houston, Tex., can be effectively utilized, however, it will be understood that various other materials such as co-knit wire and teflon (Dupont™), steel wool, polypropylene, PVDF, polyester or various other co-knit materials can also be effectively utilized in the apparatus. Various wire screen type packings may be employed where the screens are woven rather than knitted. Other acceptable coalescers include perforated sheets and expanded metals, open flow cross channel structures which are co-woven with fiberglass or other materials, such as polymers.

The coalescer material that has been wetted with sulfuric acid extracts the sulfates and sulfonic esters which are removed with the sulfuric acid via flow line 103. It has been found that the sulfuric acid contained within the alkylate reactor effluent is sufficient to wet the coalescer and remove a portion of the sulfates and sulfonic esters. However, addition of sulfuric acid about halfway up the packing makes the extraction countercurrent and more effective.

The alkylate product liquid is removed from the coalescer via flow line 102 and fed to a deisobutanizer splitter 30 containing standard distillation structure 32 where the iC4 is separated from the alkylate product and removed as overheads via flow line 104 and recycled to alkylation reactor 10. The bottoms from the deisobutanizer is fed to a debutanizer 40 which also contains standard distillation structure 42 where the nC4's are removed as overheads via flow line 106. Alkylate product is removed as bottoms via flow line 107.

EXAMPLE

Crude alkylate containing about 22% $nC_4$ was spiked with butyl hydrogen sulfate to 31.5 wppm total sulfur. This feed was treated in three ways:

1) Untreated Packing

The feed was first passed vertically downflow, at about 20 LHSV (liquid hourly space velocity)(about 600 cc) through a 6 foot by ½ inch teflon tube packed with untreated fiberglass/305 SS co-knit demister material. The effluent contained the same sulfur content as the charge.

2) $H_2SO_4$ Wetted Packing

The bottom ⅔ of the packing was wetted with 98% $H_2SO_4$ and the packing thoroughly drained. The feed was passed up flow through the packed 6 foot tube at about 20 LHSV (about 1400 cc). The effluent contained only 1.3 (at 1000 cc)–1.6 (at 1400 cc) wppm total sulfur using only ⅔ of the bed.

3) One Stage $H_2SO_4$ Treatment 65 cc of the feedstock was shaken together with 10 cc 98% $H_2SO_4$ vigorously for about 1–2 minutes and allowed to phase separate. The hydrocarbon phase contained 5.7 wppm total sulfur after the $H_2SO_4$ treatment.

The unwetted packing was seen to remove no sulfur compounds while the wetted packing removed significantly more sulfur than a single stage treatment with sulfuric acid.

The invention claimed is:

1. A process for the removal of organic sulfur compounds from a hydrocarbon stream comprising contacting said hydrocarbon stream with a coalescer which has been wetted with sulfuric acid, said sulfuric acid being added to said coalescer countercurrent to said hydrocarbon stream.

2. The process according to claim 1 wherein the hydrocarbon stream comprises the effluent from a sulfuric acid catalyzed alkylation process and the sulfuric acid is contained within the hydrocarbon stream.

3. The process according to claim 2 wherein sulfuric acid is removed from said hydrocarbon stream concurrently with the removal of organic sulfur compounds.

4. The process according to claim 1 wherein said organic sulfur compounds comprise oxygenated organic sulfur compounds.

5. A process for the treatment of the effluent from an alkylation reactor wherein a stream containing normal butene is contacted with a stream containing normal butane and isobutane in the presence of liquid sulfuric acid under conditions of temperature and pressure to produce isooctane along with sulfonates and sulfonic esters, comprising the steps of:
    (a) passing said effluent through a coalescer, said sulfuric acid being added to said coalescer countercurrent to said effluent;
    (b) concurrently in said coalescer;
        (i) removing entrained sulfuric acid from said effluent by impingement upon said coalescer;
        (ii) extracting said sulfonates and sulfonic esters in said sulfuric acid; and
        (iii) separating the effluent into a hydrocarbon effluent and a sulfuric acid effluent; and
    (c) passing the hydrocarbon effluent from said coalescer to a deisobutanizer (DIB) column where isobutane is removed as overheads and normal butane along with alkylate product is removed as bottoms.

6. The process according to claim 5 comprising:
    (d) recycling the isobutane to the alkylation reactor; and
    (e) separating the normal butane from the alkylate product.

7. A process for the treatment of the effluent from an alkylation reactor wherein a stream containing normal butene is contacted with a stream containing normal butane and isobutane in the presence of liquid sulfuric acid under conditions of temperature and pressure to produce isooctane along with sulfonates and sulfonic esters, comprising the steps of:
    (a) passing said effluent through a coalescer;
    (b) feeding sulfuric acid to said coalescer countercurrent to said effluent; and
    (c) concurrently in said coalescer;
        (i) removing entrained sulfuric acid from said effluent by impingement upon said coalescer; and
        (ii) extracting said sulfonates and sulfonic esters in said sulfuric acid.

8. The process according to claim 7 comprising:
    (d) removing sulfuric acid along with said sulfonates and sulfonic esters as a heavy liquid from said coalescer;
    (e) removing hydrocarbon liquid from said coalescer as a light liquid effluent;
    (f) passing the light liquid effluent from said coalescer to a deisobutanizer (DIB) column where isobutane is removed as overheads and normal butane along with alkylate product is removed as bottoms;
    (g) recycling the isobutane to the alkylation reactor; and
    (h) separating the normal butane from the alkylate product.

9. The process according to claim 7 wherein said coalescer comprises a mesh.

10. The process according to claim 9 wherein said coalescer comprises co-knit wire and polymeric material.

* * * * *